(12) United States Patent
End et al.

(10) Patent No.: US 7,682,404 B2
(45) Date of Patent: Mar. 23, 2010

(54) COLORING KERATIN FIBERS WITH METAL COMPLEXES

(75) Inventors: Nicole End, Oberwil (CH); Kai-Uwe Schöning, Oberwil (CH); Beate Fröhling, Grenzach-Wyhlen (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 51 days.

(21) Appl. No.: 11/919,606

(22) PCT Filed: May 3, 2006

(86) PCT No.: PCT/EP2006/061990

§ 371 (c)(1),
(2), (4) Date: Oct. 30, 2007

(87) PCT Pub. No.: WO2006/120133

PCT Pub. Date: Nov. 16, 2006

(65) Prior Publication Data

US 2009/0106915 A1    Apr. 30, 2009

(30) Foreign Application Priority Data

May 13, 2005  (EP) .................................. 05104007

(51) Int. Cl.
*A61Q 5/10*    (2006.01)

(52) U.S. Cl. .................. 8/405; 8/623; 8/628; 132/202; 132/208

(58) Field of Classification Search ..................... 8/405, 8/623, 628; 132/202, 208
See application file for complete search history.

(56) References Cited

U.S. PATENT DOCUMENTS

| 3,429,646 A * | 2/1969 | Steed ............................. 8/404 |
| 6,648,925 B1 * | 11/2003 | Mayer et al. .................... 8/405 |
| 2006/0100123 A1 | 5/2006 | Schlingloff et al. ......... 510/376 |

FOREIGN PATENT DOCUMENTS

| DE | 19852972 | 5/2000 |
| EP | 1588691 | 10/2005 |

OTHER PUBLICATIONS

STIC Search Report dated Mar. 24, 2009.*
English language abstract for DE 19852972, May 18, 2000.
English language abstract for EP 1588691, Oct. 26, 2005.
U. Heinz et al., Angew. Chem. Int. Ed. 1999, vol. 38, No. 17, pp. 2568-2570.

* cited by examiner

*Primary Examiner*—Eisa B Elhilo
(74) *Attorney, Agent, or Firm*—Mervin G. Wood; Tyler A. Stevenson

(57) ABSTRACT

The present invention concerns coloring keratin fibers, especially human hair, with colored metal complexes.

17 Claims, No Drawings

COLORING KERATIN FIBERS WITH METAL COMPLEXES

The present invention concerns coloring keratin fibers, especially human hair, with colored metal complexes.

A number of metal complexes containing multidental ligands have been known as catalysts for the oxidative coupling of hair dye precursors (DE-A-19852972; U.S. Pat. No. 6,648,925).

It has now been found that certain metal complexes may be used themselves with advantage as hair dyes.

Accordingly, the present invention relates to a non-oxidative process for coloring keratin fibers, which comprises contacting said fibers, with at least one colored metal-complex comprising a metal and a ligand of formulae (1), (2), (3), (4), (5) or (6)

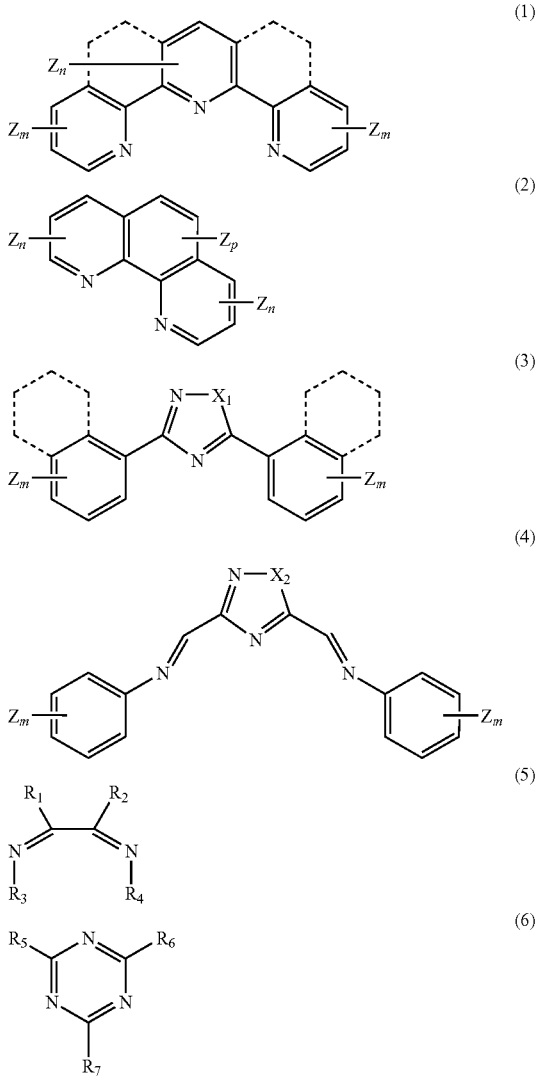

wherein $X_1$ and $X_2$ are O, S or NR, wherein R is hydrogen; unsubstituted or substituted and/or interrupted or uninterrupted alkyl; unsubstituted or substituted aryl, heteroaryl, alkylsulphonyl or arylsulphonyl;

$R_1$ and $R_2$ are independently of each other hydrogen; unsubstituted or substituted and/or interrupted or uninterrupted alkyl; unsubstituted or substituted and/or interrupted or uninterrupted cycloalkyl; unsubstituted or substituted aryl or heteroaryl; unsubstituted or substituted radical of an azo or azomethine compound;

$R_3$ and $R_4$ are independently of each other unsubstituted or substituted aryl or heteroaryl; unsubstituted or substituted radical of an azo or azomethine compound;

$R_5$, $R_6$ and $R_7$ are independently of each other unsubstituted or substituted aryl or heteroaryl; unsubstituted or substituted radical of an azo or azomethine compound; halogen; hydroxy;

$NR_8R_9$, wherein $R_8$ and $R_9$ are independently of each other unsubstituted or substituted and/or interrupted or uninterrupted alkyl or cycloalkyl; unsubstituted or substituted aryl or heteroaryl; unsubstituted or substituted radical of an azo or azomethine compound; or $R_8$ and $R_9$, together with the nitrogen atom linking them, form an unsubstituted or substituted 5-, 6- or 7-membered ring which may contain further heteroatoms;

m is 0, 1, 2, 3 or 4; it being possible when a plurality of m is present to be selected independently of each other;

n is 0, 1, 2 or 3; it being possible when a plurality of n is present to be selected independently of each other;

p is 0, 1 or 2; it being possible when a plurality of n is present to be selected independently of each other;

Z, when present, is a substituent, it being possible when a plurality of substituents Z is present for those substituents to be selected independently of each other, with the proviso that a metal-complex of $Fe^{2+}$ with 2,4,6-tris-(α-pyridyl)-1,3,5-triazine, 1,10-phenanthroline or 4'-phenyl-2-2',2"-terpyridine is excluded.

As the coloured metal complexes themselves act as the dyestuff, no additional dye is required in the present process for coloring keratin fibers, especially no dye precursor such as used in oxidative coupling reactions, e.g. aromatic phenols or aromatic amines which find use in the formation of oxidative hair colors. It is also not necessary to treat the keratine fibers with swelling agents (such as ammonia, which may cause unpleasant effects such as odor or skin irritation) beforehand to facilitate the migration of the dyes or dye precursors into the fibers.

Consequently, the present process may advantageously be carried out in the absence of a keratine swelling agent; in a preferred process, the keratin fibers or the hair is contacted with the present colored metal-complex without pre-treatment or presence of a keratin swelling agent and without presence of a dye formed in an oxidative coupling reaction or a dye precursor for such a reaction.

Preferred is a process according to the invention wherein the colored metal complexes have an extinction of at least 0.2, and more preferred of at least 0.4 in the wavelength range from 200 to 800 nm, preferably in the wavelength range from 400 to 700 nm. The ligand of formula (1)-(6) itself may be coloured and/or colour may be generated or modified by the formation of a charge transfer complex with the metal atom.

Further preferred are colored metal complexes forming a charge transfer complex.

Further preferred is a process according to the invention, wherein the colored metal complex has an extinction coefficient of at least 1000 litre×mol$^{-1}$×c$^{-1}$ in the wave length range from 200 to 800 nm, and preferably in the wavelength range from 400 to 700 nm.

The extinction and the extinction coefficient can be measured, for example, as given below: 100 mg ligand and 1 to 1.5 mol equivalent metal is mixed in 100 ml water.

1 ml of the mixture is diluted with 10 ml water to form a sample, which is analyzed by the measuring instrument, Varian Cary 50 Scan, with a Xenon lamp.

The metal used in the present invention is, for example, a transition metal, such as a metal of the 4., 5., 6. or 7. periode of the periodic system of the elements. Preferred is a metal of the 4. periode. Especially manganese, iron, copper or zinc, or nickel, manganese, iron, copper.

Preferred is the process of the invention, wherein the metal is iron or manganese, especially iron in the oxidation state II or III and manganese in the oxidation states III to V are preferred. More preferred are iron in the oxidation state II and the manganese in the oxidation state III. Most preferred is iron in the oxidation state II.

Dashed lines in formulae (1) and (3) indicate the optional presence of annellated aromatic or aliphatic 6-membered rings, which preferably are carbocyclic; for example, the compound of the formula (1) may conform to the formula

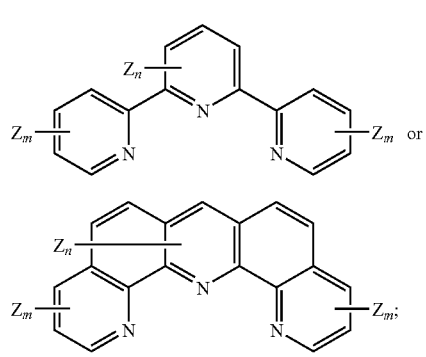

or the compound of the formula (3) may conform to the formula

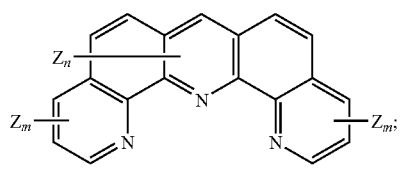

Besides the ligands (1), (2), (3), (4), (5) and (6) the metal complexes may have additional ligands, for filling up the co-ordination places of the metal, or bridging metal complexes with more than one metal.

These additional ligands are usually neutral or anionic.

Neutral ligands are for example monodonating base, such as ammonia, pyridine or water. Anionic ligands are for example halide, nitro, nitrito, nitrate, thiol or thioalcoholate, $CN^-$, $SCN^-$, acetate, trifluoracetate, formiate, carbonate, citrate, and perchlorate and complex anions, such as hexafluorophosphate. Further, oxo-ligands, peroxo-ligands or imino-ligands are possible. These latter ligands are also suitable for bridging, forming polynuclearic metal complex compounds.

Polynuclearic metal complexes mean at least two metals in a metal complex compound. These at least two metals can have different or same oxidation states and/or be of the same or different group and period of the periodic system of the elements. Preferably, at least two metals are identically.

Instead of anionic ligands the metal complex may comprise also anionic counter ions for neutralizising the cationic metal complex compounds.

Preferred anionic counter ions are for example halide, especially chloride, chlorate, perchlorate, nitrate, hydroxide, complex anions, such as hexafluorophosphate, tetrafluoroborate, sulfate, anions of carbonic acids, such as formiate, acetate, benzoate or citrate.

Further preferred is the process according to the invention, wherein the colored metal-complex comprises a metal and a ligand of formula (7)

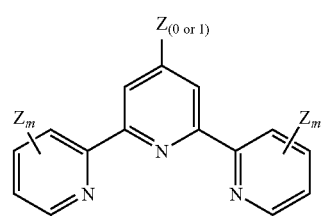

wherein
Z and m are as defined as above.

In addition preferred is the process according to the invention, wherein the colored metal-complex comprises a metal and a ligand of formula (8)

wherein
Z is as defined above.

Also further preferred is the process according to the invention, wherein the colored metal-complex comprises a metal and a ligand of formulae (9), (10), (11), (12), (13) or (14)

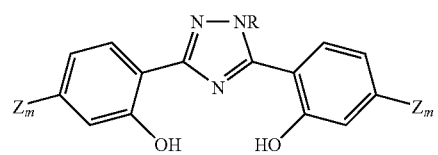

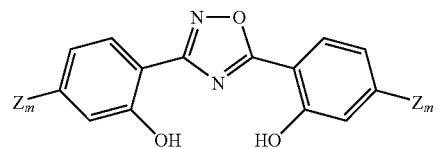

-continued

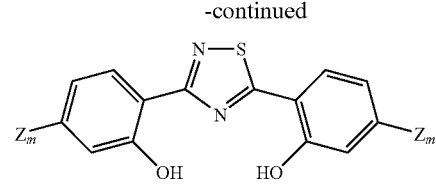
(11)

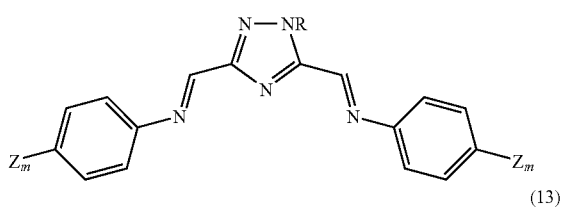
(12)

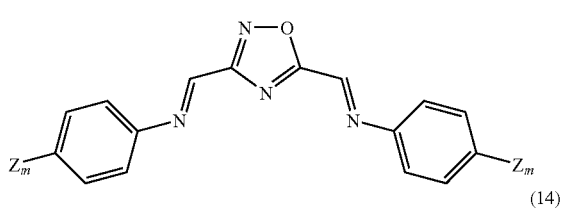
(13)

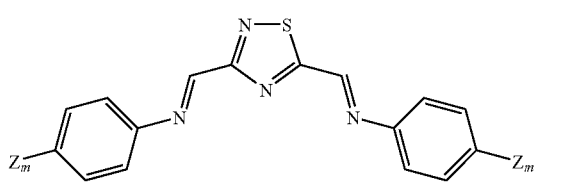
(14)

wherein

Z is defined as above, and m is 0 or 1, and R is hydrogen; unsubstituted or substituted and/or interrupted or uninterrupted $C_1$-$C_6$alkyl; unsubstituted or substituted phenyl; unsubstituted or substituted mesyl or tosyl.

Further preferred is the process according to the invention, wherein the colored metal-complex comprises a metal and a ligand of formulae (15) or (16)

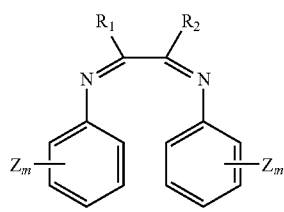
(15)

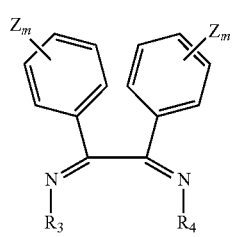
(16)

wherein

Z and m are as defined as above; and $R_1$ and $R_2$ are independently of each other hydrogen; unsubstituted or substituted and/or interrupted or uninterrupted alkyl, preferably $C_1$-$C_6$alkyl, more preferably methyl; unsubstituted or substituted and/or interrupted or uninterrupted cycloalkyl; unsubstituted or substituted phenyl or heteroaryl; unsubstituted or substituted radical of an azo or azomethine compound;

$R_3$ and $R_4$ are independently of each other unsubstituted or substituted aryl or heteroaryl; unsubstituted or substituted radical of an azo or azomethine compound.

More preferred is a process according to the invention, wherein a substituent Z is unsubstituted or substituted and/or interrupted or uninterrupted alkyl or cycloalkyl; unsubstituted or substituted aryl or heteroaryl; or unsubstituted or substituted radicals of azo or azomethine compounds; halide; cyano; guanidine; unsubstituted or substituted —$OR_8$, —$SR_8$, —$O(CO)R_8$, —$(CO)OR_8$, —$NR_{10}COR_8$, —$CONR_{10}$, —$OP(O)(OR_8)_2$, —$P(O)(OR_8)_2$, —$OS(O)_2R_8$, —$S(O)_2OR_8$, —$S(O)_2NR_8R_9$, $NR_8R_9$ or $^+NR_8R_9R_{10}$, wherein $R_8$, $R_9$ and $R_{10}$ are independently of each other hydrogen; unsubstituted or substituted and/or interrupted or uninterrupted alkyl, cycloalkyl, alkylen; unsubstituted or substituted aryl or heteroaryl; unsubstituted or substituted radical of an azo or azomethine compound; or $R_8$ and $R_9$, together with the nitrogen atom linking them, forming an unsubstituted or substituted 5-, 6- or 7-membered ring, which may contain further heteroatoms.

Furthermore preferred is a process according to the invention, wherein aryl is unsubstituted or substituted $C_5$-$C_{40}$aryl, more preferred $C_5$-$C_{20}$aryl, most preferred unsubstituted or substituted phenyl, naphthyl, anthracenyl, fluorenyl or phenanthrenyl.

In addition, more preferred is a process according to the invention, wherein heteroaryl is unsubstituted or substituted acridinyl, benzimidazolyl; benzopyrazolyl; 1,3-benzothiazolyl; 2,3-benzothiazolyl; imidazolyl; isoxazolyl; isoquinolinyl, phenanthrolinyl, terpyridinyl, triazolyl, oxazolyl, oxadiazolyl, thiadiazolyl, phenanthryl, phenazinyl, purinyl, pteridinyl, pyrazinyl, pyrazolyl, pyrimidinyl; pyridazinyl; pyridinyl; quinolinyl; thiophenyl; 1,3-thiazolyl; 1,2-thiazolyl; 1,3,4-thiadiazolyl; 1,3,5-thiadiazolyl; 1,3,4-triazolyl.

Also furthermore preferred is a process according to the invention, wherein substitutents of alkyl, cycloalkyl or alkylene are unsubstituted or substituted aryl or heteroaryl; halide; hydroxy; thiol; nitro; sulfo; cyano; guanidine; —$OR_8$, —$SR_8$, —$O(CO)R_8$, —$(CO)OR_8$, —$NR_{10}COR_8$, —$CONR_{10}$, —$O$—$P(O)(OR_8)_2$, —$P(O)(OR_8)_2$, —$OS(O)_2R_8$, —$S(O)_2OR_8$, —$S(O)_2NR_8R_9$, $NR_8R_9$ or $^+NR_8R_9R_{10}$, wherein $R_8$, $R_9$ and $R_{10}$ are independently of each other hydrogen; $C_1$-$C_8$alkyl, unsubstituted or substituted aryl or heteroaryl; unsubstituted or substituted radical of an azo or azomethine compound; or $R_8$ and $R_9$, together with the nitrogen atom linking them, forming an unsubstituted or substituted 5-, 6- or 7-membered ring which may contain further heteroatoms.

In addition, more preferred is a process according to the invention, wherein substitutents of aryl or heteroaryl are alkyl, cycloalkyl; unsubstituted or substituted radicals of azo or azomethine compounds; halide; hydroxy; thiol; nitro; sulfo; cyano; guanidine; unsubstituted or substituted —$OR_8$, —$SR_8$, —$O(CO)R_8$, —$(CO)OR_8$, —$NR_{10}COR_8$, —$CONR_{10}$, —$O$—$P(O)(OR_8)_2$, —$P(O)(OR_8)_2$, —$OS(O)_2R_8$, —$S(O)_2OR_8$, —$S(O)_2NR_8R_9$, $NR_8R_9$ or $^+NR_8R_9R_{10}$, wherein $R_8$, $R_9$ and $R_{10}$ are independently of each other hydrogen; unsubstituted or substituted and/or interrupted or uninterrupted alkyl, cycloalkyl, alkylen; unsubstituted or substituted aryl or heteroaryl, or $R_8$ and $R_9$, together with the nitrogen atom linking them, form an unsubstituted or substituted 5-, 6- or 7-membered ring which may contain further heteroatoms.

Further definitions and preferences according to the invention are given below:

According to the invention alkyl is for example $C_1$-$C_{18}$alkyl, preferably $C_1$-$C_6$alkyl, and more preferably $C_1$-$C_4$alkyl, and —S-alkyl is for example —S—$C_1$-$C_{18}$alkyl, preferably —S—$C_1$-$C_6$alkyl, and more preferably —S—$C_1$-$C_4$alkyl, and —O-alkyl is for example —O—$C_1$-$C_{18}$alkyl, preferably —O—$C_1$-$C_6$alkyl, and more preferably —O—$C_1$-$C_4$alkyl; and alkylen is for example $C_1$-$C_{18}$alkylene, preferably $C_1$-$C_6$alkylene, and more preferably $C_1$-$C_4$alkylene.

$C_1$-$C_{18}$alkyl is, for example, methyl, ethyl, propyl, isopropyl, n-butyl, sec-butyl, tert-butyl, n-pentyl, 2-pentyl, 3-pentyl, 2,2'-dimethylpropyl, cyclopentyl, cyclohexyl, n-hexyl, n-octyl, 1,1',3,3'-tetramethylbutyl or 2-ethylhexyl, nonyl, decyl, undecy, dodecyl, tredecyl, tetradecyl, pentadecyl, hexadecyl, heptadecyl or octadecyl.

$C_1$-$C_6$alkyl is, for example, methyl, ethyl, propyl, isopropyl, n-butyl, sec-butyl, tert-butyl, n-pentyl, 2-pentyl, 3-pentyl, 2,2'-dimethylpropyl, cyclopentyl, cyclohexyl or n-hexyl.

$C_1$-$C_4$alkyl is, for example, methyl, ethyl, propyl, isopropyl, n-butyl, sec-butyl or tert-butyl.

$C_1$-$C_4$alkyl is, for example, methyl, ethyl, propyl, isopropyl, n-butyl, sec-butyl or tert-butyl.

$C_1$-$C_6$alkylene is, for example, methylen, ethylene propylen, isopropylen, n-butylen, sec-butylen, tert-butylen, n-pentylen, 2-pentylen, 3-pentylen, 2,2'-dimethylpropylen, cyclopentylen, cyclohexylen or n-hexylen.

Alkylsulphonyl is, for example, $C_1$-$C_{18}$alkylsulphonyl, preferably $C_1$-$C_6$alkylsulphonyl and more preferred $C_1$-$C_4$alkylsulphonyl, which can be substituted, unsubstituted, interrupted or not interrupted, linear or branched, and preferably alkylsulphonyl is mesyl.

Alkyl or cycloalkyl generally is unsubstituted or substituted and/or uninterrupted or interrupted by, for example, interrupted by at least one heteroatom such as —O—, —S—, —($SO_2$)— or —($NR_{10}$)—, wherein $R_{10}$ has the above given definition. Cycloalkyl may be mono, bi, tri or polycyclic. Preferred cycloalkyl is $C_5$-$C_{20}$cycloalkyl such as cyclopentyl, cyclohexyl, cycloheptyl, cyclooctyl, cyclononyl, cyclodecyl, cycloundecyl or cyclododecyl. Preferred interrupted cycloalkyl is the radical of pyrazol, oxazol, morpholino, piperidino, and piperazino.

Arylsulphonyl is, for example, unsubstituted or substituted $C_5$-$C_{40}$arylsulphonyl, more preferred $C_5$-$C_{20}$arylsulphonyl, and most preferred tosyl, naphthylsulphonyl, anthracenylsulphonyl, fluorenylsulphonyl or phenanthrenylsulphonyl, and especially most preferred is tosyl.

Azo or azomethine compounds each of them represent classes of dyes, which are, as for example, defined in the Color Index by the Society of Textile Chemist and Colorist. Any radical in the form of an azo or azomethine compound may be formed from one of these known dyes by abstraction of a hydrogen atom or an alkyl moiety such as a methyl group. Preferred are radicals which are unsubstituted azo or azomethine compounds. Preferred azo compound is Basic Orange 31 or Basic Red 51 and preferred azomethine compound is Basic Yellow 87.

Halogen is fluoro, chloro, bromo or iodide. Preferred halogen is fluoro, chloro or bromo, and more preferred halogen is fluoro or chloro.

$NR_8R_9$ is an amine, which is preferably a compound of formulae:

—N($R_9$)—($C_1$-$C_6$alkylene)—$R_{13}$, —N($R_9$)—($C_1$-$C_6$alkylene)—$NR_{10}R_{11}$;

—N[($C_1$-$C_6$alkylene)—$NR_{10}R_{11}$]$_2$; —N($R_9$)—($C_1$-$C_6$alkylene)—$N^{\oplus}R_{10}R_{11}R_{12}$; —N[($C_1$-$C_6$alkylene)-$N^{\oplus}R_{10}OR_{11}R_{12}$]$_2$; —N($R_9$)—N—$R_{10}R_{11}$ or —N($R_9$)—$N^{\oplus}R_{10}R_{11}R_{12}$, wherein $R_9$ is hydrogen or $C_1$-$C_{18}$alkyl, aryl or heteroaryl; wherein $R_{10}$, $R_{11}$ and $R_{12}$ are each independently of the other hydrogen, $C_1$-$C_{18}$alkyl, aryl or heteroaryl, or $R_{10}$ and $R_{11}$, together with the nitrogen atom linking them, form an unsubstituted or substituted 5-, 6- or 7-membered ring which may contain further hetero-atoms; and $R_{13}$ is OH, SH, —O—$C_1$-$C_6$alkyl or —S—$C_1$-$C_6$alkyl, aryl or heteroaryl.

More preferred are amines of formulae, —N($R_9$)—($C_1$-$C_6$alkylene)-$R_{13}$, wherein $R_{13}$ is OH, SH, —O—$C_1$-$C_6$alkyl or —S—$C_1$-$C_6$alkyl, aryl or heteroaryl;

and most preferred are amines of formulae:

—NH—($C_1$-$C_2$alkylene)—OH, —N($CH_3$)—($C_1$-$C_6$alkylene)—OH, —N($C_2H_5$)—($C_1$-$C_6$alkylene)—OH; —N($CH_3$)$CH_2CH_2$—OH; —NH$CH_2CH_2$—OH;

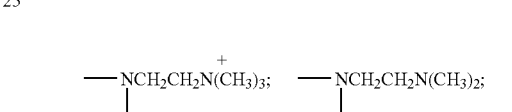

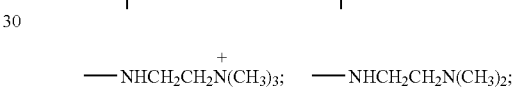

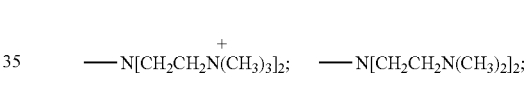

—N[$CH_2CH_2CH_2N(CH_3)_2$]$_2$ and

—$\overset{+}{N}$[$CH_2CH_2CH_2N(CH_3)_3$]$_2$.

Especially most preferred are amines of formulae: —N($CH_3$)$CH_2CH_2$—OH; —NH$CH_2CH_2$—OH.

Further, preferred are cyclic amines of formula, $NR_{10}R_{11}$ or $NR_8R_9$ wherein $R_{10}$ and $R_{11}$ or $R_8$ and $R_9$, together with the nitrogen atom linking them, form an unsubstituted or substituted 5-, 6- or 7-membered ring which may contain further heteroatoms, such as pyrazol, oxazol, morpholino, piperidino, piperazino.

Especially preferred are cyclic amines of formulae:

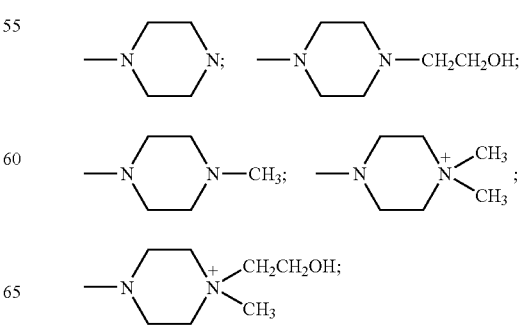

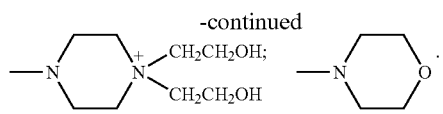

Examples of cations that come into consideration in the present invention include alkali metal cations, such as lithium, potassium, sodium and especially sodium, alkaline earth metal cations, such as magnesium and calcium, and ammonium cations. The alkali metal cations are preferred, especially sodium.

The present invention further concerns a metal complex comprising a metal and a ligand of formula (3a)

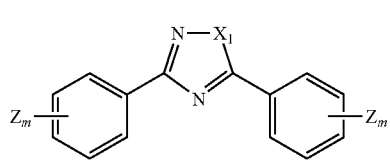

(3a)

or a ligand of formula (4a)

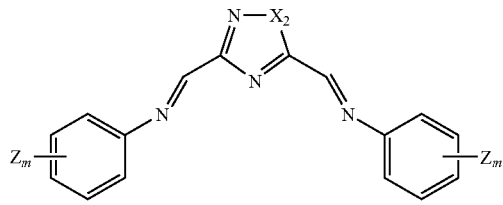

(4a)

wherein $X_1$, $X_2$, Z and m are defined as given above, and a ligand of formula (6)

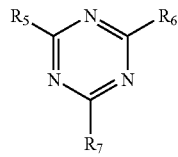

(6)

$R_5$ is unsubstituted or substituted heteroaryl or unsubstituted or substituted radical of an azo or azomethine compound; and $R_6$ and $R_7$ are independently of each other unsubstituted or substituted aryl or heteroaryl; unsubstituted or substituted radical of an azo or azomethine compound; halogen; hydroxy; $NR_8R_9$, wherein $R_8$ and $R_9$ are independently of each other unsubstituted or substituted and/or interrupted or uninterrupted alkyl or cycloalkyl; unsubstituted or substituted aryl or heteroaryl; unsubstituted or substituted radical of an azo or azomethine compound; or $R_8$ and $R_9$, together with the nitrogen atom linking them, form an unsubstituted or substituted 5-, 6- or 7-membered ring which may contain further heteroatoms.

In addition, the present invention further concerns a ligand of formula (3a)

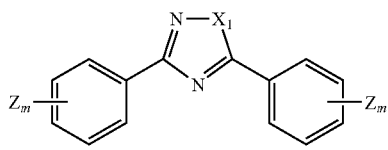

(3a)

or a ligand of formula (4a)

(3b)

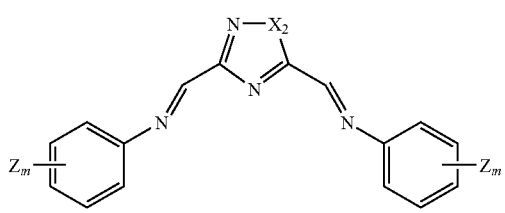

(4a)

wherein $X_1$, $X_2$, Z and m are defined as given above, or a ligand of formula (6)

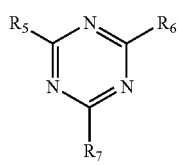

(6)

wherein $R_5$ is 1,10-phenanthrolinyl; unsubstituted or substituted radical of an azo or azomethine compound; and $R_6$ and $R_7$ are independently of each other unsubstituted or substituted aryl or heteroaryl; unsubstituted or substituted radical of an azo or azomethine compound; halogen; hydroxy; $NR_8R_9$, wherein $R_8$ and $R_9$ are independently of each other unsubstituted or substituted and/or interrupted or uninterrupted alkyl or cycloalkyl; unsubstituted or substituted aryl or heteroaryl; unsubstituted or substituted radical of an azo or azomethine compound; or $R_8$ and $R_9$, together with the nitrogen atom linking them, form an unsubstituted or substituted 5-, 6- or 7-membered ring which may contain further heteroatoms.

Definitions and preferences given for metal complexes of formulae (3), (9), (10) and (11) apply also for the metal complexes and ligands of formula (3a).

Definitions and preferences given for metal complexes of formulae (4), (12), (13) and (14) apply also for the metal complexes and ligands of formula (4a).

The ligands of the present invention can be prepared in analogy to known processes.

The ligands of formula (1) can for example be prepared as given below: two parts of pyridine-2-carboxylic acid ester and one part of acetone can be reacted with sodium hydride and the intermediate, a 1,3,5-triketone, obtained after aqueous working-up can be reacted with ammonium acetate to synthesize the central pyridine ring. The corresponding pyridone derivatives are obtained, which can be converted into the chlorine compounds by reaction with a chlorinating agent, such as PCl$_5$/POCl$_3$. Reactions of such compounds with amines, if desired in the presence of an excess of transition metal salts, such as iron or manganese, in order to accelerate the substitution, yield amine-substituted terpyridines. Such preparation processes are described, for example, in J. Chem. Soc., Dalton Trans. 1990, 1405-1409 and New. J. Chem. 1992, 16, 855-867.

The ligand of formula (2) can be prepared for example in analogy to the synthesis of Skraup by contacting derivatives of o-phenylendiamine or derivatives of 8-aminochinoline with nitrobenzene in glycerine in the presence of concentrated sulphuric acid.

Compounds of formula (3) are usually obtained in analogy to known processes, for the preparation of 1,2,4-thiadiazole, 1,2,4-oxadiazole or 1,2,4-triazole.

Compounds of formula (3) are preferably prepared by a process, as described in WO 03/053986, comprising contacting a compound of formula (20), with a compound of formula (21)

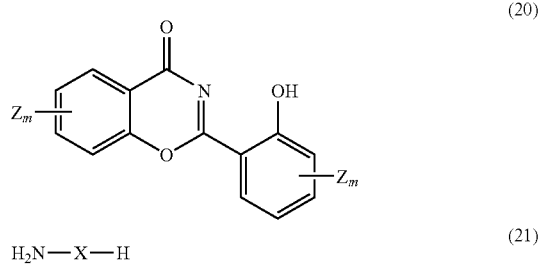

(20)

(21)

wherein
Z and m are defined as given above for compound of formula (3).

The reaction is preferably carried out in a solvent, for example ethanol, by boiling for several hours under reflux.

Further preferred is a process for the preparation of ligands of formula (3), as described in Tetrahedron, 45, 1989, on page 4599, and in Journal of Organic Chemistry, 64, 1999, on page 6989, which process comprises reacting two mol equivalents of compounds of formula (22)

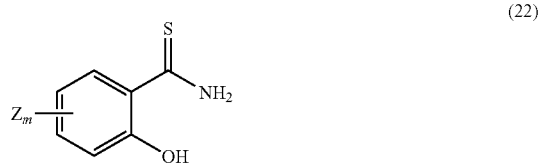

(22)

wherein
Z and m are defined as given above for compound of formula (3); or by contacting two mol equivalents of compounds of formula (23)

(23)

with a compound of formula (24)

(24)

wherein
Z and m are defined as given above for compound of formula (3).

The compounds of formula (4) can for example be prepared by a process comprising
a) contacting a compound of formula (25)

(25)

wherein
X$_1$ and X$_2$ are O, S or NR, wherein R is hydrogen; unsubstituted or substituted and/or interrupted or uninterrupted alkyl; unsubstituted or substituted aryl, heteroaryl, alkylsulphonyl or arylsulphonyl,
with an amine of formula (26)

(26)

Z and m are defined as given above for compound of formula (4).

The compounds of formula (5) are for example usually prepared by condensation of mono- or dicarbonyl compounds with amines.

The compounds of formula (6) are for example usually prepared by substitution of trichlor- or trifluortriazine with a desired nucleophil.

The dyes of the invention (i.e. metal-complexes comprising a ligand selected from formulae (1), (2), (3), (4), (5) and (6)) are suitable for colouring keratin-containing fibres. "Keratin-containing fibres" are to be understood as wool, furs, feathers and, especially, human hair. The keratin-containing fibres may be pretreated. For example, hair may first be treated with a shampoo or peroxide.

The present invention concerns the use of at least one metal complex comprising a ligand selected from formulae (1), (2), (3), (4), (5) or (6) as defined above, and/or at least one ligand of formulae (3a), (4a) or (6a) as defined above for colouring keratinic fibers.

A further embodiment of the present invention concerns compositions comprising metal complexes according to the present invention, and/or at least one ligand according to the present invention.

The metal complex comprising a ligand selected from formulae (1), (2), (3), (4), (5) and (6) is present in the compositions according to the invention preferably in an amount of from 0.001% to 5%, especially from 0.01% to 1%, based on the total weight of the dyeing composition.

It often is convenient first to form the complex and then applying it to the keratin-containing fibres. The complex may be formed by reacting an aqueous solution of a salt of a metal, especially a transition metal, with a solution of a ligand.

Alternatively, the solution of the metal salt and the solution of the ligand are applied to the keratin-containing fibres consecutively so as to form the complex in situ. Usually, the sequence of addition does not effect the result.

The common anions, which are used in the metal salts are for example chloride, iodide, perchlorate, fluoroborate, sulphate, nitrate, acetate, citrate, tartrate, high molecular weight sulphonates and sulphates, sulphite, high molecular weight carboxylate or nitritre; and preferably, chloride, sulphate, nitrateee, acetate, citrate, tartrate, sulphite, acids or nitrite are used.

Some oxidation states of metals used in the metal complexes are not stable in aqueous solutions. It may therefore be of advantage to form unstable oxidation states of metals in situ, just before the preparation of the dyeing solution, by reduction or oxidation of more stable oxidation states of the metal. For example iron in the oxidation state II can be formed by reduction from iron in the oxidation state III. Suitable reducing agents are for example ascorbic acid, glucose or alkali metal sulfites, such as sodium sulfite or potassium sulfite.

For the colored complex to be stable during application, it is of advantage to use a solution of a slightly acidic, neutral or slightly basic pH value. More precisely, the pH during application should be in the region of 4 to 9, preferably between pH 5.5 and 8.5. It may be of further advantage to use a buffered solution. A buffer solution is a solution of a substance that minimizes changes in the pH when an acid or base is added to the solution and may for example contain alkali phosphates, citrates, acetates, or tris(hydroxymethyl)aminomethane salts. Examples of suitable agents for adjusting the pH of the solution of the metal complex or the ligand are ammonia, alkali hydroxide, alkali carbonates, organic bases such as amines or, if required, inorganic acids such as hydrochloric acid or organic acids such as citric acid.

The colouration of hair often is satisfactorily carried out at normal room temperature, i.e. in a temperature range of about 18 to 25° C., especially at about 20° C. Hair is suitably treated at a temperature conventionally used for the colouration of hair. Preferably the temperature is less then 40° C. More preferably, the temperature is in the range of 20-30° C.

If the metal complex is sparingly soluble in water, water-miscible solvents and solubilizers may be used such as alcohols, ketones, glycols, and non-ionic and amphoteric surface-active agents. Typical examples are ethanol, n-propanol, isopropanol, n-butanol, isobutanol, dioxane, acetone, propylene glycol, polyethylene glycols, glycerol, sorbitol, polyoxyethylene sorbitans, polyoxyethylene phenols, betaine detergents, polyoxyethylene amines and ethoxylated lanolins.

The multiplicity of shades and the color fastness of the dyes used in accordance with the invention may be increased by combination with other non-oxidative dyes used in the field of hair-dyeing compositions, e.g. with direct dyes or nitro dyes; direct dyes may be cationic or uncharged.

For example, the metal complex comprising a ligand selected from formula (1), (2), (3), (4), (5) and/or (6) according to the invention may readily be used in combination with other dyes used in the colouring of hair such as
  nitrobenzene derivatives, as described in WO 99/20235, especially page 26, line 7 to page 30, line 15,
  cationic dyes, especially those described in particular on pages 11 to 27 of WO 95/01772. Especially suitable are Basic Yellow 87, Basic Orange 31 and/or Basic Red 51.

For use on human hair, the dyeing compositions can usually be incorporated into an aqueous cosmetic carrier. Suitable aqueous cosmetic carriers include, for example, creams, emulsions, gels and also surfactant-containing foaming solutions, e.g. shampoos or other preparations, that are suitable for use on keratin-containing fibres. Such forms of use are described in detail in Research Disclosure 42448 (August 1999). If necessary, it is also possible to incorporate the dyeing compositions into anhydrous carriers, as described, for example, in U.S. Pat. No. 3,369,970, especially column 1, line 70 to column 3, line 55. The dyeing compositions according to the invention are also excellently suitable for the colouring method described in DE-A-3 829 870 using a colouring comb or a colouring brush.

The dyeing compositions according to the invention may furthermore comprise any active ingredient, additive or adjuvant known for such preparations. The dyeing compositions in many cases comprise at least one surfactant. There are suitable in principle anionic and also zwitterionic, ampholytic, non-ionic and cationic surfactants. In many cases, however, it has proved advantageous to select the surfactants from anionic, zwitterionic and non-ionic surfactants. The dyeing compositions of the invention usually contain the present metal complex in an amount from about 0.1 to about 5% by weight, preferably 0.2 to 2% by weight, for example 0.1-0.9, or 1.1-2.0% by weight of the composition or formulation.

Anionic surfactants suitable for use in the preparations according to the invention include all anionic surface-active substances that are suitable for use on the human body. Such substances are characterised by an anionic group that imparts water solubility, for example a carboxylate, sulfate, sulfonate or phosphate group, and a lipophilic alkyl group having approximately from 10 to 22 carbon atoms. In addition, glycol or polyglycol ether groups, ester, ether and amide groups and also hydroxy groups may be present in the molecule. The following are examples of suitable anionic surfactants, each in the form of sodium, potassium or ammonium salts or mono-, di- or tri-alkanolammonium salts having 2 or 3 carbon atoms in the alkanol group:
  linear fatty acids having from 10 to 22 carbon atoms (soaps),
  ether carboxylic acids of formula $R-O-(CH_2-CH_2-O)_x-CH_2-COOH$, in which R is a linear alkyl group having from 10 to 22 carbon atoms and x=0 or from 1 to 16,
  acyl sarcosides having from 10 to 18 carbon atoms in the acyl group,
  acyl taurides having from 10 to 18 carbon atoms in the acyl group,
  acyl isothionates having from 10 to 18 carbon atoms in the acyl group,
  sulfosuccinic mono- and di-alkyl esters having from 8 to 18 carbon atoms in the alkyl group and sulfosuccinic monoalkylpolyoxyethyl esters having from 8 to 18 carbon atoms in the alkyl group and from 1 to 6 oxyethyl groups,
  linear alkane sulfonates having from 12 to 18 carbon atoms,
  linear α-olefin sulfonates having from 12 to 18 carbon atoms,
  α-sulfo fatty acid methyl esters of fatty acids having from 12 to 18 carbon atoms,
  alkyl sulfates and alkyl polyglycol ether sulfates of formula $R'-O(CH_2-CH_2-O)_x-SO_3H$, in which R' is a preferably linear alkyl group having from 10 to 18 carbon atoms and x'=0 or from 1 to 12,
  mixtures of surface-active hydroxysulfonates according to DE-A-3 725 030, especially page 3, lines 40 to 55, sulfated hydroxyalkylpolyethylene and/or hydroxyalkylenepropylene glycol ethers according to DE-A-3 723 354, especially page 4, lines 42 to 62, sulfonates of unsaturated fatty acids having from 12 to 24 carbon atoms and from 1 to 6 double bonds according to DE-A-3 926 344, especially page 2, lines 36 to 54, esters of tartaric acid and citric acid with alcohols which are addition products of approximately from 2 to 15 molecules of ethylene oxide and/or propylene oxide with fatty alcohols having from 8 to 22 carbon atoms.

Preferred anionic surfactants are alkyl sulfates, alkyl polyglycol ether sulfates and ether carboxylic acids having from 10 to 18 carbon atoms in the alkyl group and up to 12 glycol ether groups in the molecule, and also especially salts of saturated and especially unsaturated $C_8$-$C_{22}$carboxylic acids, such as oleic acid, stearic acid, isostearic acid and palmitic acid.

Surface-active compounds that carry at least one quaternary ammonium group and at least one —$COO^{(-)}$ or —$SO_3^{(-)}$ group in the molecule are termed zwitterionic surfactants. Zwitterionic surfactants that are especially suitable are the so-called betaines, such as the N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having from 8 to 18 carbon atoms in the alkyl or acyl group and also cocoacylaminoethylhydroxyethylcarboxymethyl glycinate. A preferred zwitterionic surfactant is the fatty acid amide derivative known by the CTFA name cocamidopropyl betaine.

Ampholytic surfactants are to be understood as meaning surface-active compounds that, in addition to a $C_8$-$C_{18}$-alkyl or -acyl group, contain at least one free amino group and at least one —$COOH$ or —$SO_3H$ group in the molecule and are capable of forming internal salts. Examples of suitable ampholytic surfactants include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each having approximately from 8 to 18 carbon atoms in the alkyl group. Ampholytic surfactants to which special preference is given are N-cocoalkylaminopropionate, cocoacylaminoethylaminopropionate and $C_{12}$-$C_{18}$acylsarcosine.

Non-ionic surfactants contain as the hydrophilic group, for example, a polyol group, a polyalkylene glycol ether group or a combination of polyol and polyglycol ether groups.

Such compounds are, for example:
addition products of from 2 to 30 mol of ethylene oxide and/or from 0 to 5 mol of propylene oxide with linear fatty alcohols having from 8 to 22 carbon atoms, with fatty acids having from 12 to 22 carbon atoms and with alkylphenols having from 8 to 15 carbon atoms in the alkyl group, $C_{12}$-$C_{22}$ fatty acid mono- and di-esters of addition products of from 1 to 30 mol of ethylene oxide with glycerol, $C_8$-$C_{22}$alkyl-mono- and -oligo-glycosides and ethoxylated analogues thereof, addition products of from 5 to 60 mol of ethylene oxide with castor oil and hydrogenated castor oil, addition products of ethylene oxide with sorbitan fatty acid esters,—addition products of ethylene oxide with fatty acid alkanolamides.

Examples of cationic surfactants that can be used in the hair-treatment compositions according to the invention are especially quaternary ammonium compounds. Preference is given to ammonium halides, such as alkyltrimethylammonium chlorides, dialkyldimethylammonium chlorides and trialkylmethylammonium chlorides, for example cetyltrimethylammonium chloride, stearyltrimethylammonium chloride, distearyidimethylammonium chloride, lauryidimethylammonium chloride, lauryidimethylbenzylammonium chloride and tricetylmethylammonium chloride. Further cationic surfactants that can be used in accordance with the invention are quaternised protein hydrolysates.

Also suitable in accordance with the invention are cationic silicone oils, such as, for example, the commercially available products Q2-7224 (manufacturer: Dow Corning; a stabilised trimethylsilylamodimethicone), Dow Corning 929 emulsion (comprising a hydroxylamino-modified silicone, which is also referred to as amodimethicone), SM-2059 (manufacturer: General Electric), SLM-55067 (manufacturer: Wacker) and also Abil®-Quat 3270 and 3272 (manufacturer: Th. Goldschmidt; diquaternary polydimethylsiloxanes, quaternium-80).

Alkylamidoamines, especially fatty acid amidoamines, such as the stearylamidopropyldimethylamine obtainable under the name Tego Amid® 18, are distinguished not only by a good conditioning action but also especially by their good biodegradability Quaternary ester compounds, so-called "esterquats", such as the methyl hydroxyalkyldialkoyloxyalkylammonium methosulfates marketed under the trade mark Stepantex®, are also very readily biodegradable.

An example of a quaternary sugar derivative that can be used as cationic surfactant is the commercial product Glucquat®100, according to CTFA nomenclature a "lauryl methyl gluceth-10 hydroxypropyl dimonium chloride".

The alkyl-group-containing compounds used as surfactants may be single substances, but the use of natural raw materials of vegetable or animal origin is generally preferred in the preparation of such substances, with the result that the substance mixtures obtained have different alkyl chain lengths according to the particular starting material used.

The surfactants that are addition products of ethylene and/or propylene oxide with fatty alcohols or derivatives of such addition products may either be products having a "normal" homologue distribution or products having a restricted homologue distribution. "Normal" homologue distribution is to be understood as meaning mixtures of homologues obtained in the reaction of fatty alcohol and alkylene oxide using alkali metals, alkali metal hydroxides or alkali metal alcoholates as catalysts. Restricted homologue distributions, on the other hand, are obtained when, for example, hydrotalcites, alkali metal salts of ether carboxylic acids, alkali metal oxides, hydroxides or alcoholates are used as catalysts. The use of products having restricted homologue distribution may be preferred.

Examples of further active ingredients, adjuvants and additives are as follows:

non-ionic polymers, for example vinylpyrrolidone/vinyl acrylate copolymers, polyvinylpyrrolidone and vinylpyrrolidone/vinyl acetate copolymers and polysiloxanes, cationic polymers, such as quaternised cellulose ethers, polysiloxanes having quaternary groups, dimethyidiallylammonium chloride polymers, copolymers of dimethyidiallylammonium chloride and acrylic acid, as available commercially under the name Merquat® 280 and the use of which in hair colouring is described, for example, in DE-A-4 421 031, especially page 2, lines 20 to 49, or EP-A-953 334, especially page 27, line 17 to page 30, line 11, acrylamide/dimethyidiallylammonium chloride copolymers, diethyl-sulfate-quaternised dimethylaminoethyl methacrylate/vinyl pyrrolidone copolymers, vinylpyrrolidone/imidazolinium methochloride copolymers, quaternised polyvinyl alcohol, zwitterionic and amphoteric polymers, such as, for example, acrylamidopropyl-trimethylammonium chloride/acrylate copolymers and octylacrylamide/methyl methacrylate/tert-butylaminoethyl methacrylate/2-hydroxypropyl methacrylate copolymers, anionic polymers, such as, for example, polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert-butyl acrylamide terpolymers, thickeners, such as agar, guar gum, alginates, xanthan gum, gum arabic, karaya gum, locust bean flour, linseed gums, dextrans, cellulose derivatives, e.g. methyl cellulose, hydroxyalkyl cellulose and carboxymethyl cellulose, starch fractions and derivatives, such amylose, amylopectin and dextrins, clays, e.g. bentonite or fully synthetic hydrocolloids such as, for example, polyvinyl alcohol, structuring agents, such as glucose and maleic acid, hair-conditioning compounds, such as phospholipids, for example soya lecithin, egg lecithin, and cephalins, silicone oils, and also conditioning compounds, for example such as those described in DE-A-19 729 080, especially page 2, lines 20 to 49, EP-A-834 303, especially page 2, line 18 to page 3, line 2, or EP-A-312 343, especially page 2, line 59 to page 3, line 11, protein hydrolysates, especially elastin, collagen, keratin, milk protein, soya protein and wheat protein hydrolysates, condensation products thereof with fatty acids and also quaternised protein hydrolysates, perfume oils, dimethyl isosorbitol and cyclodextrins, solubilisers, such as ethanol, isopropanol, ethylene glycol, propylene glycol, glycerol and diethylene glycol, anti-dandruff active ingredients, such as piroctones, olamines and zinc Omadine, further substances for adjusting the pH value, active ingredients such as panthenol, pantothenic acid, allantoin, pyrrolidonecarboxylic acids and salts thereof, plant extracts and vitamins, cholesterol, light stabilisers and UV absorbers, as described, for example, in EP-A-819 422, especially page 4, lines 34 to 37, consistency regulators, such as sugar esters, polyol esters or polyol alkyl ethers, fats and waxes, such as spermaceti, beeswax, montan wax, paraffins, fatty alcohols and fatty acid esters, fatty alkanolamides, polyethylene glycols and polypropylene glycols having a molecular weight of from 150 to 50 000, for example such as those described in EP-A-801 942, especially page 3, lines 44 to 55, complexing agents, such as EDTA, NTA and phosphonic acids, swelling and penetration substances, such as polyols and polyol ethers, as listed extensively, for example, in EP-A-962 219, especially page 27, lines 18 to 38, for example glycerol, propylene glycol, propylene glycol monoethyl ether, butyl glycol, benzyl alcohol, carbonates, hydrogen carbonates, guanidines, ureas and also primary, secondary and tertiary phosphates, imidazoles, tannins, pyrrole, opacifiers, such as latex, pearlising agents, such as ethylene glycol mono- and distearate, propellants, such as propane-butane mixtures, $N_2O$, dimethyl ether, $CO_2$ and air, and also antioxidants.

The constituents of the aqueous carrier are used in the preparation of the dyeing compositions according to the invention in the amounts customary for that purpose; for example emulsifiers are used in concentrations of from 0.5 to 30% by weight and thickeners in concentrations of from 0.1 to 25% by weight of the total dyeing composition.

To colour keratin-containing fibres, especially to colour human hair, the dyeing compositions are usually applied to the hair in an amount of from 10 to 100 g in the form of the aqueous cosmetic carrier, left there for approximately 30 minutes and then rinsed off or washed off with a commercially available hair shampoo.

EXAMPLE

Unless specified otherwise, parts and percentages relate to weight.

Example 1

2-(Methyl-[2,2';6'2"]terpyridine-4'yl-amino)-ethanol

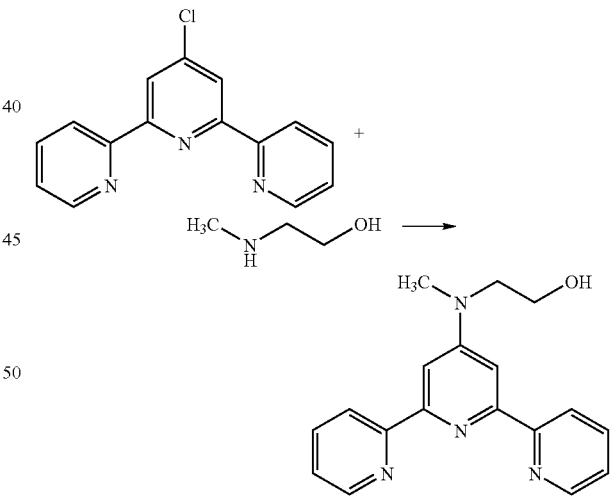

129 g (1.72 mol) 2-methylamino-ethanol and 390 mg (2.86 mmol) zinc(II)-chloride are successively added to a suspension of 15.3 g (57.2 mmol) 4'-chloro-2,2';6,2"-terpyridine in 100 ml 2-methyl-2-butanol. The reaction mixture is refluxed for 2.5 days. A brown suspension is obtained, which is evaporated under vacuum to a yellow-brown solid product. 100 ml water is added to this product and stirred at room temperature for 20 minutes. Then, the obtained mixture is filtrated and the filter residue dried for 12 hours at (45° C., 10 mbar). 14.8 g (84%) of 2-(methyl-[2,2';6'2"]terpyridine-4'yl-amino)-ethanol as colourless solid product is obtained.

Application: Example 2

Preparing of the Ligand Solution (1a):
A 12.5 mM solution is prepared by dissolving 38 mg 2-(methyl-[2,2';6'2"]terpyridine-4'yl-amino)-ethanol in 20 ml ethanol p.a.

Preparing of the Fe (III) Solution (2):
A 60 mM solution is prepared by dissolving 1.6 g Fe(III)-chlorid hexahydrate in 100 ml water.

Preparing of the Ascorbic Acid Solution (3):
A 60 mM solution is prepared by dissolving 1.06 g ascorbic acid in 100 ml water.

Preparing of the Dyeing-Solution (4a):
300 µl of a ligand solution (1a), 60 µl Fe(III)-solution (2), and 70 µl ascorbic acid solution (3) are added to 10 ml water and stirred. The obtained solution is violet.

Dyeing Process:
A blonde, a blonde bleached, a middle blonde and a bleached hair tress are treated in each case with 10 ml of the dyeing solution (4a) for 10 min. Afterwards the tresses are shampooed and dried on a glass plate.

Result:

| Quality of hair | color |
|---|---|
| blonde | violet |
| blonde bleached | violet |
| middle blonde | violet |
| bleached | violet |

Application: Example 3

Preparing of the Ligand Solution (1b):
A 12.5 mM solution is prepared by dissolving 49 mg 1,10-phenanthrolin-5-ylamine in 20 ml ethanol p.a.

Preparing of the Dyeing-Solution (4b):
300 µl ligand solution (1b), 60 µl Fe(III)-solution (2) according to example 2, and 70 µl ascorbic acid solution (3) according to example 2 are mixed in 10 ml water.
The obtained solution is orange.

Dyeing Process:
A blonde, a blonde bleached, a middle blonde and a bleached hair tress are treated in each case with 10 ml of the dyeing solution (4b) for 45 min. Afterwards the tresses are shampooed and dried on a glass plate.

Result:

| Quality of hair | colour |
|---|---|
| blonde | orange |
| blonde bleached | orange |
| middle blonde | orange |
| bleached | orange |

The invention claimed is:

1. A process for coloring keratin fibers, which comprises contacting said fibers, with at least one colored metal-complex comprising a metal and a ligand of formulae (1), or (2),

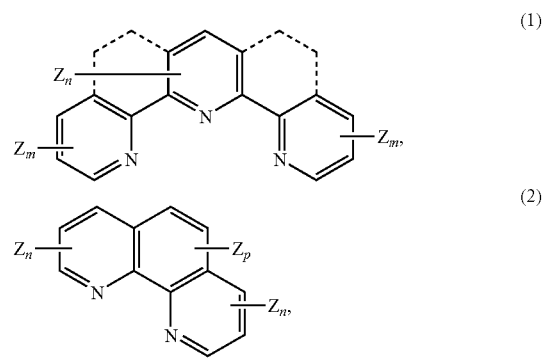

wherein m is 0, 1, 2, 3 or 4; it being possible when a plurality of m is present to be selected independently of each other;

n is 0, 1, 2 or 3; it being possible when a plurality of n is present to be selected independently of each other;

p is 0, 1 or 2; it being possible when a plurality of n is present to be selected independently of each other;

Z, when present, is unsubstituted or substituted and/or interrupted or uninterrupted alkyl or cycloalkyl; unsubstituted or substituted aryl or heteroaryl; or unsubstituted or substituted radicals of azo or azomethine compounds; halogen; hydroxyl; thiol; nitro; sulfo; cyano; guanidine; unsubstituted or substituted $-OR_8$, $-SR_8$, $-O(CO)R_8$, $-(CO)OR_8$, $-NR_{10}COR_8$, $-CONR_{10}$, $-OP(O)(OR_8)_2$, $-P(O)(OR_8)_2$, $-OS(O)_2R_8$, $-S(O)_2OR_8$, $-S(O)_2NR_8R_9$, $NR_8R_9$ or $^+NR_8R_9R_{10}$, wherein $R_8$, $R_9$ and $R_{10}$ are independently of each other hydrogen; unsubstituted or substituted and/or interrupted or uninterrupted alkyl, cycloalkyl, alkylen; unsubstituted or substituted aryl or heteroaryl; unsubstituted or substituted radical of an azo or azomethine compound; or $R_8$ and $R_9$, together with the nitrogen atom linking them, form an unsubstituted or substituted 5-, 6- or 7-membered ring which may contain further heteroatoms;

with the proviso that a metal-complex of $Fe^{2+}$ with 2,4,6-tris-(α-pyridyl)-1,3,5-triazine, 1,10-phenanthroline or 4'-phenyl-2-2',2"-terpyridine is excluded;

wherein said process is carried out in the absence of a dye precursor, and is a process wherein the keratin fibers or the hair is contacted with the colored metal-complex without pre-treatment or presence of a keratin swelling agent and the colored metal-complex is the only dye used.

2. The process according to claim 1, wherein the metal is iron or manganese.

3. The process according to claim 2, wherein the metal is iron in the oxidation state II.

4. The process according to claim 1, wherein the colored metal complex is applied in a solution having a pH in the range 4 to 9.

5. The process according to claim 1, wherein the contacting is carried out below 40° C.

6. The process according to claim 1 which comprises contacting said fibers, with a colored metal-complex comprising a metal and a ligand of formula (7)

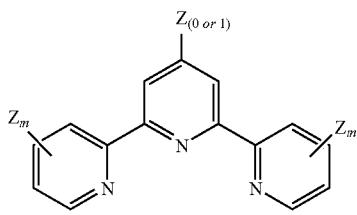

wherein
Z and m are as defined in claim 1.

7. The process according to claim 1 which comprises contacting said fibers, with a colored metal-complex comprising a metal and a ligand of formula (8)

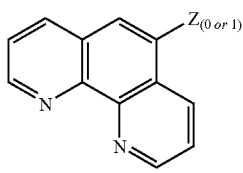

wherein
Z is as defined in claim 1.

8. The process according to claim 1 wherein aryl, wherever mentioned, is selected from the group consisting of unsubstituted or substituted phenyl, naphthyl, anthracenyl, fluorenyl and phenanthrenyl.

9. The process according to claim 1, wherein any substituent of alkyl, cycloalkyl or alylen is selected from unsubstituted or substituted aryl or heteroaryl; halogen; hydroxy; thiol; nitro; sulfo; cyano; guanidine; —$OR_8$, —$SR_8$, —O(CO)$R_8$, —(CO)$OR_8$, —$NR_{10}COR_8$, —$CONR_{10}$, —OP(O)(OR$_8$)$_2$, —P(O)(OR$_8$)$_2$, —OS(O)$_2R_8$, —S(O)$_2OR_8$, —S(O)$_2NR_8R_9$, $NR_8R_9$ or $^+NR_8R_9R_{10}$, wherein $R_8$, $R_9$ and $R_{10}$ are independently of each other hydrogen; $C_1$-$C_8$alkyl, aryl or heteroaryl; a radical of an azo or azomethine compound; or $R_8$ and $R_9$, together with the nitrogen atom linking them, form an unsubstituted or substituted, preferably aromatic, 5-, 6- or 7-membered ring which may contain a further heteroatom; any substituent of aryl or heteroaryl is selected from alkyl, cycloalkyl; a radical of an azo or azomethine compound; halogen; hydroxy; thiol; nitro; sulfo; cyano; guanidine; unsubstituted or substituted —$OR_8$, —S—$R_8$, —O—(CO)—$R_8$, —(CO)—$OR_8$, —$NR_{10}$CO—$R_8$, —$CONR_{10}$, —O—P(O)(OR$_8$)$_2$, —P(O)(OR$_8$)$_2$, —OS(O)$_2R_8$, —S(O)$_2OR_8$, —S(O)$_2NR_8R_9$, $NR_8R_9$ or $^+NR_8R_9R_{10}$, wherein $R_8$, $R_9$ and $R_{10}$ are independently of each other hydrogen; unsubstituted or substituted and/or interrupted or uninterrupted alkyl, cycloalkyl, alkylene; any alkyl is $C_1$-$C_{18}$alkyl, any alkylene is selected from $C_1$-$C_{18}$alkylene,
any cycloalkyl is selected from $C_5$-$C_{20}$cycloalkyl, and
any interrupting moiety is selected from —O—, —S—, —(SO$_2$)— or —(NR$_{10}$)—, wherein $R_{10}$ is alkyl or cycloalkyl.

10. A composition comprising at least one metal complex or at least one ligand according claim 1.

11. The composition according to claim 10 wherein said composition is incorporated into a solution, shampoo, conditioner, gel or emulsion.

12. The composition according to claim 10 which is a dyeing composition containing the metal complex in an amount from 0.1 to 5% by weight of the composition.

13. The process according to claim 5, wherein the contacting is carried out in the temperature range of 20-30° C.

14. The process according to claim 1 wherein heteroaryl, wherever mentioned, is selected from the group consisting of unsubstituted or substituted acridinyl, benzimidazolyl; benzopyrazolyl; 1,3-benzothiazolyl; 2,3-benzothiazolyl; imidazolyl; isoxazolyl; isoquinolinyl, phenanthrolinyl, terpyridinyl, triazolyl, oxazolyl, oxadiazolyl, thiadiazolyl, phenanthryl, phenazinyl, purinyl, pteridinyl, pyrazinyl, pyrazolyl, pyrimidinyl; pyridazinyl; pyridinyl; quinolinyl; thiophenyl; 1,3-thiazolyl; 1,2-thiazolyl; 1,3,4-thiadiazolyl; 1,3,5-thiadiazolyl; and 1,3,4-triazolyl.

15. A composition comprising at least one metal complex or at least one ligand wherein said metal complex comprising a metal and a ligand of formula (3a)

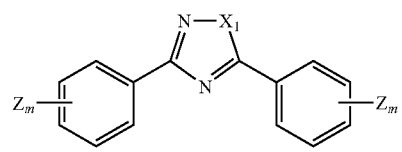

or
a ligand of formula (4a)

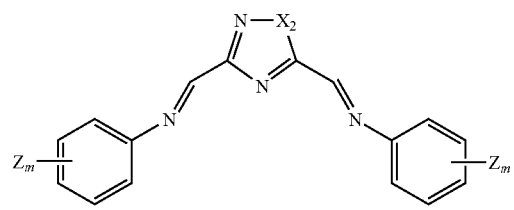

wherein
substituent Z is unsubstituted or substituted and/or interrupted or uninterrupted alkyl or cycloalkyl; unsubstituted or substituted aryl or heteroaryl: or unsubstituted or substituted radicals of azo or azomethine compounds; halogen; hydroxyl; thiol; nitro; sulfo; cyano: guanidine; unsubstituted or substituted —$OR_8$, —$SR_8$, —O(CO)$R_8$, —(CO)$OR_8$, —$NR_{10}COR_8$, —$CONR_{10}$, —OP(O)(OR$_8$)$_2$, —P(O)(OR$_8$)$_2$, —OS(O)$_2R_8$, —S(O)$_2OR_8$, —S(O)$_2NR_8R_9$, $NR_8R_9$ or $^+NR_8R_9R_{10}$, wherein $R_8$, $R_9$ and $R_{10}$ are independently of each other hydrogen; unsubstituted or substituted and/or interrupted or uninterrupted alkyl, cycloalkyl, alkylen; unsubstituted or substituted aryl or heteroaryl; unsubstituted or substituted radical of an azo or azomethine compound; or $R_8$ and $R_9$, together with the nitrogen atom linking them, forming an unsubstituted or substituted 5-, 6- or 7-membered ring, which may contain further heteroatoms;

$X_1$ and $X_2$ are O, S or NR, wherein R is hydrogen; unsubstituted or substituted and/or interrupted or uninterrupted alkyl; unsubstituted or substituted aryl, heteroaryl. alkylsulphonyl or arylsulphonyl;

m is 0,1, 2, 3 or 4; it being possible when a plurality of m is present to be selected independently of each other;

and
a ligand of formula (6)

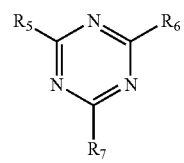

wherein $R_5$ is unsubstituted or substituted heteroaryl or unsubstituted or substituted radical of an azo or azomethine compound; and $R_6$ and $R_7$ are independently of each other unsubstituted or substituted aryl or heteroaryl; unsubstituted or substituted radical of an azo or azomethine compound; halogen; hydroxyl; $NR_8R_9$, wherein $R_8$ and $R_9$ are independently of each other unsubstituted or substituted and/or interrupted or uninterrupted alkyl or cycloalkyl; unsubstituted or substituted aryl or heteroaryl; unsubstituted or substituted radical of an azo or azomethine compound; or $R_8$ and $R_9$, together with the nitrogen atom linking them, form an unsubstituted or substituted 5-, 6- or 7-membered ring which may contain further heteroatoms, with the proviso that a metal-complex of $Fe^{2+}$ with 2,4,6-tris-(α-pyridyl)-1,3,5-triazine, 1,10-phenanthroline or 4'-phenyl-2-2',2''-terpyridine is excluded.

16. The composition according to claim 15 wherein said composition is incorporated into a solution, shampoo, conditioner, gel or emulsion.

17. The composition according to claim 15 which is a dyeing composition containing the metal complex in an amount from 0.1 to 5% by weight of the composition.

* * * * *